United States Patent
Ritter et al.

(10) Patent No.: US 10,046,101 B2
(45) Date of Patent: Aug. 14, 2018

(54) EXTRACORPOREAL BLOOD TREATMENT MACHINE COMPRISING LEAKAGE DETECTION AND METHOD OF DETECTING LEAKAGES IN DIALYSIS FLUID SYSTEMS

(71) Applicant: B. BRAUN AVITUM AG, Melsungen (DE)

(72) Inventors: Kai-Uwe Ritter, Melsungen (DE); Oliver Schulz, Lohfelden (DE)

(73) Assignee: B. BRAUN AVITUM AG, Melsungen (DE)

(*) Notice: Subject to any disclaimer, the term of this patent is extended or adjusted under 35 U.S.C. 154(b) by 0 days.

(21) Appl. No.: 15/719,049

(22) Filed: Sep. 28, 2017

(65) Prior Publication Data

US 2018/0015216 A1    Jan. 18, 2018

Related U.S. Application Data

(62) Division of application No. 14/590,505, filed on Jan. 6, 2015, now Pat. No. 9,801,994.

(30) Foreign Application Priority Data

Jan. 10, 2014    (DE) .......................... 10 2014 100 260

(51) Int. Cl.
*A61M 1/36* (2006.01)
*A61M 1/14* (2006.01)

(52) U.S. Cl.
CPC ............ *A61M 1/3607* (2014.02); *A61M 1/14* (2013.01); *A61M 2205/15* (2013.01); *A61M 2205/3327* (2013.01)

(58) Field of Classification Search
CPC .. A61M 1/14; A61M 1/3607; A61M 2205/15; A61M 2205/3327
See application file for complete search history.

(56) References Cited

U.S. PATENT DOCUMENTS

| 2005/0101901 A1 | 5/2005 | Gura |
| 2009/0012454 A1 | 1/2009 | Childers |
| 2011/0272337 A1 | 11/2011 | Palmer |

FOREIGN PATENT DOCUMENTS

| WO | 2012042481 A2 | 4/2012 |

OTHER PUBLICATIONS

German Search Report for German Application No. DE 10 2014 100 260.1, dated Nov. 13, 2014, with translation—15 Pages.
European Search Report for European Application No. EP15150353.9, dated May 27, 2015—9 Pages.
Non Final Office Action for U.S. Appl. No. 14/590,505, dated Mar. 1, 2017, 6 pages.

(Continued)

*Primary Examiner* — John Kim
(74) *Attorney, Agent, or Firm* — RatnerPrestia

(57) ABSTRACT

The invention relates to an extracorporeal blood treatment machine, such as a dialysis machine, comprising leakage detection as well as to a method of detecting leakages in the dialysis fluid circuit of a dialysis machine, wherein at least part of the dialysis fluid system to be monitored in terms of leakage is accommodated in a hermetically sealed housing and the housing is or can be ventilated in a controlled manner, and wherein a parameter, such as the air humidity of the air flowing into the housing is compared to a corresponding parameter, preferably air humidity of the air flowing out of the housing.

11 Claims, 1 Drawing Sheet

(56) References Cited

OTHER PUBLICATIONS

Notice of Allowance for U.S. Appl. No. 14/590,505, dated Jul. 3, 2017, 13 pages.
Entire patent prosecution history of U.S. Appl. No. 14/590,505, filed Jan. 6, 2015, entitled Extracorporeal Blood Treatment Machine Comprising Leakage Detection and Method of Detecting Leakages in Dialysis Fluid Systems.

EXTRACORPOREAL BLOOD TREATMENT MACHINE COMPRISING LEAKAGE DETECTION AND METHOD OF DETECTING LEAKAGES IN DIALYSIS FLUID SYSTEMS

CROSS REFERENCE TO RELATED APPLICATIONS

This application is a divisional of U.S. application Ser. No. 14/590,505, filed Jan. 6, 2015, which claims priority to German Application Number DE 10 2014 100 260.1, filed Jan. 10, 2014, the contents of each of which are incorporated by reference herein.

FIELD OF THE INVENTION

The invention relates to an extracorporeal blood treatment machine, preferably dialysis machine comprising leakage detection and to a method of detecting leakages in the dialysis fluid or dialysate system of a dialysis machine.

Leakages occurring in the dialysis fluid system of a dialysis machine, especially in the balancing circuit of a dialysis machine are critical, as dialysis fluid escaped from the system is missing in the total balance and by reason of the balancing principle a corresponding quantity of fluid is withdrawn from the patient. Such withdrawal of fluid can be critical already in small quantities depending on the patient's weight and/or condition.

BACKGROUND

At present it is known to carry out a single pressure test or cyclic pressure tests for detecting leakages in the dialysis fluid system. As a rule, they take place before a treatment. It is a drawback in this context that leakages occurring as late as during treatment cannot be detected or can be detected as late as during the preparation of a subsequent treatment. Carrying out cyclic pressure tests during a treatment disadvantageously results in delays of the course of therapy and thus in an efficient reduction of the duration of therapy, which has to be compensated by longer treatment periods for each patient. In general, it is a drawback that the accuracy in pressure tests is dependent on the amount of pressure as well as the pressure dwell time, which may question the reliability of the established values.

Furthermore, from the state of the art solutions are known in which leakage fluid is collected in an appropriate reservoir of the dialysis machine. The liquid level in the reservoir is detected via a fill level sensor or the like. It is a drawback in these solutions that apart from dialysis fluid escaping from the system further fluid such as condensation water may accumulate in the reservoir, thus resulting in errors in determining the quantity of dialysis fluid escaped from the system. Also in the inverse case that it is not the total quantity of dialysis fluid escaped from the system due to leakage which is collected in the container, for example because a particular share thereof evaporates, errors occur when the quantity escaped from the system is determined.

Basically state-of-the-art leakage detection is somewhat unsecure and inaccurate. There is the risk that minor leakage points that may already have serious effects depending on the patient are not yet or only inaccurately detected. Usually state-of-the-art systems only work reliably at higher leakage rates. Known leakage detections partly cause a loss of time with and reduction in quality of dialysis treatments.

SUMMARY OF THE INVENTION

Based on the afore-described state of the art, it is an object underlying the present invention to eliminate the afore-stated drawbacks, especially to provide a possibility of leakage detection in the dialysis fluid system of an extracorporeal blood treatment machine, preferably a dialysis machine, which works comparatively safely, accurately and reliably in the case of small leakage quantities, by which continuous monitoring of the system in terms of leakage is possible, especially also during a current treatment substantially without disturbance thereof, which causes or requires no substantial extension or interruption of the treatment and is comparatively inexpensive.

The afore-mentioned object and further objectives of the present invention are achieved by an extracorporeal blood treatment machine, preferably a dialysis machine, comprising the features described herein and by a method including the method steps described herein.

According to aspects of the invention, an object according to a first aspect is achieved by an extracorporeal blood treatment machine, preferably a dialysis machine, comprising a housing having at least one first ventilation aperture and at least one second ventilation aperture, the housing being formed to be hermetically sealed against the ambience with the exception of the ventilation apertures and in the housing at least part of a dialysis fluid system to be detected/tested in terms of leakage, preferably the entire dialysis fluid system being accommodated, wherein at least one vent is provided with which air can be conveyed or is conveyed from one of the ventilation apertures (suction aperture) through the housing to the other (exhaust aperture) of the ventilation apertures, the dialysis machine moreover including at least one measuring unit by which the humidity of the air flowing into and out of the housing via the ventilation apertures can be determined or is determined.

Furthermore, an object is achieved according to another aspect of the invention by a method of detecting leakages in a dialysis fluid system of a dialysis machine in which a housing having at least one first ventilation aperture (suction aperture) and at least one second ventilation aperture (exhaust aperture) and for the rest being hermetically sealed (fluid-tight) against the environment comprises at least a part of the dialysis fluid system to be detected/monitored in terms of leakage, preferably comprises the entire dialysis fluid system, wherein the housing is ventilated via the ventilation apertures, preferably ventilated exclusively via the ventilation apertures, so that air and/or humidity can be prevented from penetrating except via the ventilation apertures, wherein parameters of state such as especially air mass or air mass flow, temperature and/or humidity etc. of inlet air fed into the housing as well as outlet air discharged from the housing are detected and preferably compared, and wherein a humidity input into the housing based on leakage at the dialysis fluid system inside the housing is determined from the difference of these values.

The part of the dialysis fluid system of the machine accommodated in the housing and to be detected in terms of leakage is hermetically shielded against the environment, preferably by the housing. Thus it is shielded against external humidity sources. Exceptions are the dialysis fluid system of the machine in the case of leakage as well as air entering into the housing via the ventilation apertures. In other words, the housing is designed so that air can penetrate the housing only via the/any ventilation aperture. The humidity or the humidity input of air penetrating the housing (in a controlled manner) via the ventilation apertures is detected and balanced according to the teaching of the invention. In this way a defined self-contained air path can be formed in which at least one parameter (representing the air humidity or indicating the air humidity) of the air flowing through the housing, preferably of the inlet air flowing toward the interior of the housing and/or the outlet air flowing out of the interior of the housing can be determined, e.g. via a humidity sensor. Thus the housing forms sort of a balance sheath, wherein all humidity inputs and outputs into and out of the housing can be detected (by sensors), with the exception of humidity originating from leakages of the dialysis fluid system which can be determined indirectly via balancing, however.

In the case of leakage of dialysis fluid from the (entire) dialysis fluid system or from the part thereof to be monitored in terms of leakage, the leaked dialysis fluid necessarily enters into the interior of the housing. Here the escaped dialysis fluid evaporates, thus resulting in an increase in the air humidity inside the housing and consequently in the exhaust air jet flow out of the housing. Preferably means are provided which cause rapid and complete evaporation of leakage fluid, e.g. a nonwoven or an additional blower promoting the desired evaporation by additional and well-directed air motion. From the difference of the parameters of inlet and outlet air representing or indicating air humidity it can be determined whether and possibly in which quantity humidity additionally enters into the ventilation system, especially into the housing. Humidity introduced via inlet air is necessarily detected and taken into account. When parameters of inlet and outlet air are determined with sufficient accuracy, already minimal leakage rates can be established with the aid of the present invention.

A dialysis machine basically includes two circuits, i.e. the extracorporeal blood circuit and the dialysis fluid circuit. The extracorporeal blood circuit and the dialysis fluid circuit are communicated via a dialyser. From the dialysis fluid circuit physiological fluid, especially dialysis fluid, can be supplied to the extracorporeal blood circuit, e.g. to compensate for excessive (undesired) fluid losses of the patient. By the dialysis fluid system in accordance with the present description the part of the machine is to be understood which guides physiological fluid, especially dialysis fluid, in particular the dialysis fluid circuit as well as components and ducts branching off the former and communicating the same with the extracorporeal blood circuit, or parts thereof.

In a preferred embodiment of the invention the at least one venting means includes a blower or is formed by the same. Such blower can be provided anyway under certain circumstances in the dialysis machine and preferably can serve for a parallel or simultaneous cooling of the machine. Especially advantageously, the housing can be vented by the venting means, i.e. air can be conveyed out of the housing by the venting means, preferably into the environment. In the housing a vacuum is formed vis-à-vis the environment so that the probability of inadvertent air leak except via the ventilation means or the outlet air aperture can be reduced by which air leak detection of humidity introduced into the air inside the housing due to leakage could be falsified or prevented.

It is within the scope of the invention to use a housing having only one inlet air aperture and only one outlet air aperture. The housing may also include plural inlet air apertures and/or plural outlet air apertures. According to aspects of the invention, parameters of the airflows are monitored and detected at all inlet and outlet air apertures.

According to an embodiment of the invention at least one parameter of the air flowing through the housing, preferably of the inlet airflow flowing into the housing and/or of the outlet airflow flowing out of the housing is continuously detected. It is moreover within the scope of the invention to detect one or each parameter continuously or cyclically. In particular, at least one parameter or all parameters can be detected in discrete measuring cycles. Between the individual measuring cycles there can be time intervals of equal or different length. Ventilation of the housing during these time intervals advantageously may serve not only for detecting a parameter for leakage detection but (especially also exclusively) for cooling the housing interior and the dialysis machine.

According to aspects of the invention, the volume flow and/or the mass flow and/or the flow rate of the air passed through the housing can be constant. According to a special configuration of the invention, these parameters of the air guided through the housing can be varied, however. Such variation advantageously can be carried out in a cycle-specific manner in the case of discrete measuring cycles. For example, according to aspects of the invention the volume flow or the mass flow or the flow rate of the air flowing through the housing can be set or controlled during particular measuring cycles and/or time intervals between said measuring cycles to such measure that, on the one hand, sufficient cooling of the machine and, on the other hand, sort of a basic detection of leakages are possible for detecting major leakages with sufficiently great safety.

In order to be able to safely detect even small leakages that cannot be detected in the case of a volume or mass flow ensuring sufficient cooling of the machine (i.e. a volume/mass flow which is relatively high), as the increase in humidity of the air quantity flowing through the housing would be too small for being detected, a measuring cycle can be interspersed in which the airflow guided through the housing can be set to be very small (smaller than the value set as a standard) or as small as possible. During such measuring cycle sufficient cooling of the machine might no longer be completely provided, however in this way also small leakages can be safely detected, as due to the small volume/mass flow and the low flow rate, respectively, they cause an increase in humidity of the airflow guided through the housing in the case of leakage which is sufficient or distinct for being detected.

In order to be able to detect minimal leakages in an embodiment of the invention the airflow through the housing is stopped for a particular period of time, especially prior to a measuring cycle, e.g. by completely down-regulating the venting means. During this period of time in which no air is flowing through the housing, even in the case of minimal leakages an increase (enrichment) in humidity of the air quantity present in the housing occurs, which can be easily and safely determined during subsequent measurement. In total, the invention advantageously allows detecting leakages almost independently of the quantity and/or the mass or volume flow of the escaping dialysis fluid over a wide range of mass and volume flows. It is possible to reliably and quickly detect leakages of different magnitude, even small and minimal leakages. Cooling of the machine can be operated without any substantial impairment.

According to an embodiment of the invention, the detected values of the parameters of inlet and/or outlet air are utilized to optimize the cooling and/or the sound level of the machine.

According to another embodiment of the invention, in the housing a nonwoven or the like can be arranged. The latter is advantageously suited and arranged to preferably completely absorb escaped dialysis fluid and promptly discharge the same via its large surface at a high evaporation rate. The nonwoven or the like is preferably disposed at such positions where leakage is suspected. In accordance with another configuration of the invention, such suspect positions can of preference be monitored, for example by directing the airflow specifically to the position of the suspected leakage, for instance with corresponding airflow guiding means or with another blower or ventilation unit.

In an advantageous embodiment of the method of the invention the system can be calibrated, especially before the start of treatment. It can be checked whether fluid is provided inside the housing of the dialysis machine. In this case after a first ventilation cycle of the housing the direction of the flow through the housing is reversed. In the event that inside the housing no fluid is provided, an offset of the sensor used for detecting parameters of the inflowing or outflowing air quantity is equal in the normal direction of flow and in the reversed direction of flow through the housing. If fluid, especially dialysis fluid, has escaped from the dialysate system due to a leak and is present in the interior of the housing, the two offset values measured during calibration are different. The sensor at the respective outlet air aperture indicates the higher value. When the offset remains constant in both directions of flow through the housing, it can be compensated by calibrating the sensor. Of particular advantage, such checking or calibration by reversing the direction of flow of the air through the housing can also be carried out during a treatment without impairing the latter.

According to an embodiment of the invention, the direction of flow through the housing is repeatedly alternated, especially regularly alternated. This can be done in parallel to the usual treatment operation. In this way, a drift of the sensor/sensors can be detected more or less promptly and can be corrected, if desired. Moreover, pollution of the inlet and/or outlet air aperture can be reduced by repeated reversal of the direction of flow through the housing. Finally a plausibility check can be performed by reversing the direction of flow through the housing 4 after additional humidity has been determined in the housing. In this way it can be determined whether an increase in the measuring value was in fact caused by dialysis fluid entered from the dialysis fluid system into the housing or else is based only on a measuring error or on increasing air humidity of the ambient air. Thus the number of false alarms can advantageously be reduced and the reliability of the system and the method, respectively, can be improved.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
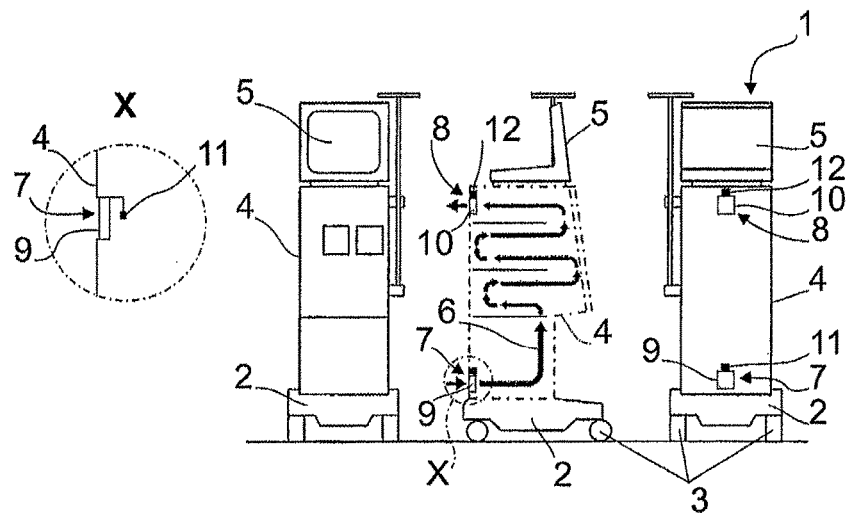
FIG. 1 shows a first embodiment of an extracorporeal blood treatment machine, preferably dialysis machine according to aspects of the invention.

FIG. 1 shows a dialysis machine 1 according to aspects of the invention in a front view, a rear view and a partly cut side view. Preferably it includes a movable base 2 having rollers 3. On the base a housing 4 hermetically sealed (fluid-tight) against the ambience is arranged which in turn supports a displaying and operating unit 5. In the hermetically sealed housing 4 at least one dialysis fluid system not shown in detail in the Figure is arranged/accommodated. It includes/guides a dialysis fluid which is processed in a known manner with the dialysis fluid system.

The housing 4 is ventilated, inter alia, for cooling purposes in that airflow is guided through an inlet air aperture 7 into the machine 1, through the housing 4 and out of the housing 1 via an outlet air aperture 8 separate herefrom. In the central representation of FIG. 1 the flow path 6 through the housing 4 is schematically indicated with meander-like arrows. The flow path 6 is configured so that the airflow guided through the housing 4 preferably flows through all areas of the housing 4. It can be especially configured so that air is specifically guided into areas in which leakages are suspected to occur or into areas in which leaking fluid preferably accumulates.

In the inlet air aperture 7 a first blower 9 is arranged. In the outlet air aperture 8 a second blower 10 is arranged. In the illustrated flow direction of the air through the housing 4 (flow path 6) the airflow is preferably caused by the second blower 10 conveying air out of the housing 4. The first blower 9 is not driven or is driven at a lower capacity than the first blower 10 so that in the housing 4 a vacuum vis-à-vis the ambience is formed. In this way it is ensured that air can only get out of the housing via the second blower 10 and the outlet air aperture 8 and only additional humidity in the airflow due to leakage in the dialysis fluid system can be safely detected.

The detection of the humidity of the inflowing air is brought about in the shown flow path 6 with a first humidity sensor 11 arranged in or adjacent to the inlet air aperture 7. The humidity of the outlet airflow leaving the machine 1 is detected with a second humidity sensor 12 arranged in or adjacent to the outlet air aperture 8. From comparison of the humidity values established by the two sensors 11, 12 conclusions to humidity additionally introduced into the housing 4 hermetically sealed against the ambience, for instance due to leakage of the dialysis fluid system, can be drawn, as will be described in detail hereinafter.

The dialysis machine shown in FIG. 1 can be ventilated in the inverse direction as represented. Upon reversal of the flow direction 6 air flows through the outlet air aperture 8 into the housing 4 and leaves the same again via the inlet air aperture 7. In this case the ventilation is preferably effectuated with the first blower 9 so that—as afore-described—in the housing 4 a vacuum is prevailing vis-à-vis the ambience.

Figure 2:
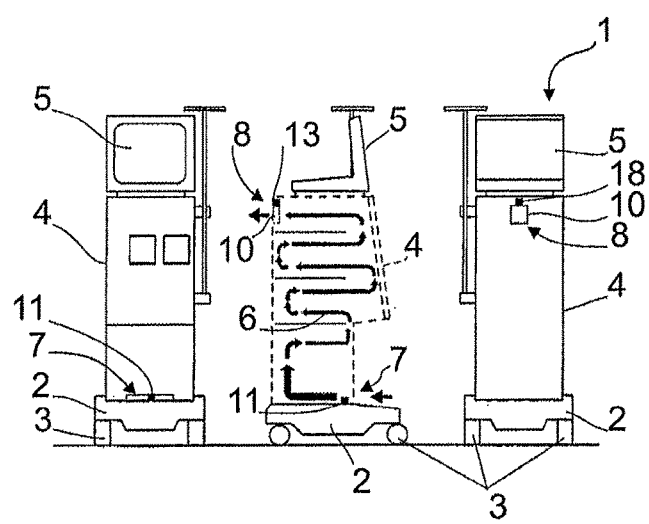
FIG. 2 shows a second embodiment of an extracorporeal blood treatment machine, preferably dialysis machine according to aspects of the invention.

FIG. 2 illustrates a second embodiment of the dialysis machine 1 in a front view, a rear view and a partly cut side view. Since this Figure substantially resembles the embodiment of FIG. 1, the foregoing description of this embodiment is referred to and hereinafter substantially only deviations therefrom will be described.

The housing 4 equally includes an inlet air aperture 7 and an outlet air aperture 8. In the outlet air aperture 8 a blower 13 is arranged as the only blower of this embodiment. In or adjacent to the inlet air aperture 7 a first humidity sensor 11 is disposed. In or adjacent to the outlet air aperture 8 finally a second humidity sensor 12 is disposed. with the humidity sensors 11, 12 the humidity of the airflow passing through the inlet air aperture 7 and the outlet air aperture 8, respectively, is measured.

The passage of the embodiment shown in FIG. 2 usually takes place as indicated with the arrows concerning the flow path 6. The blower 13 works in the suction mode and vents the housing 4 by sucking air from the interior of the housing into the atmosphere. However, it can also be ventilated in the inverse direction as illustrated. For this purpose, the blower 13 is operated in the blow mode conveying air from the atmosphere into the housing 4.

Figure 3:
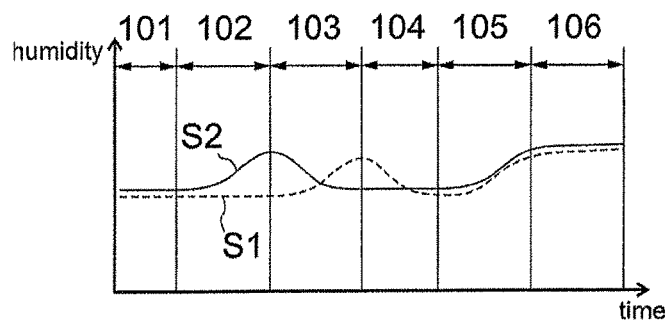
FIG. 3 shows a signal curve for humidity values in the case of measurements in the apparatus according to FIGS. 1 and 2, respectively.

FIG. 3 illustrates the theoretical signal course during measurement of the humidity values with the two humidity sensors 11, 12 of the embodiments of the FIGS. 1 and 2. The broken curve S1 represents the signal course of the first humidity sensor 11, the continuous curve S2 shows the signal course of the second humidity sensor 12. The humidity values measured by the humidity sensors are applied to the abscissa of the diagram of FIG. 3. The time is applied to the ordinate.

In a first time interval 101 the two humidity sensors 11 and 12 are calibrated. During a following time interval 102 leakage occurs in the dialysis fluid system of the machine 1. Dialysis fluid escaping (leaking) from the same enters into the housing 4 hermetically sealed against the ambience, evaporates there and results in an increase in the air humidity inside the housing 4 as well as vis-à-vis the ambient air, which increase can only be detected, due to the flow direction in the housing 4, by the second humidity sensor 12 arranged in the outlet air aperture 8. The first humidity sensor 11 in the inlet air aperture in the time interval 102 continuously detects the humidity (which is constant as a rule) of the ambient air flowing into the housing 4. This is clearly reflected in the course of the signal curves S1 and S2: S1 remains substantially constant while S2 (clearly) increases in the course of the time interval 102.

In a subsequent time interval 103, after detecting the increase of the signal S2 of the second sensor 12, a plausibility check is made by reversing the flow direction through the housing 4 as described with reference to FIG. 1 or 2. Then no more air from the housing 4 but ambient air (usually having constant air humidity) is applied to the second sensor 12. Its signal S2 therefore decreases to the normal value of the ambient air in the course of the time interval 103. On the other hand, in the time interval 103 outlet air flowing out of the housing 4 is applied to the first sensor 11. In the case of leakage in the dialysis fluid system entailing penetration of dialysis fluid into the housing 4, the sensor 11 determines an increase in the air humidity inside the housing 4. If the increase of the signal S2 of the second sensor during the time interval 102 is based on a sensor error or the like, however, i.e. if no dialysis fluid has entered into the housing 4, the sensor 11 would detect no increased humidity in the housing 4 during the time interval 103 and its signal S1 would remain constant. A first indication of leakage therefore can be easily checked, whereby fault alarms can be reduced or prevented and the reliability of the system is increased.

In other words, the two sensors 11, 12 are alternately operated as inlet and outlet sensors at the separate ventilation apertures so as to exclude or reduce possible measuring errors.

If there is leakage—and this case is shown in FIG. 3—the leak is eliminated. This takes place at the beginning of a further time interval 104. Due to the continued ventilation of the housing 4 in the time interval 104 the air humidity and thus the signal S1 are slowly decreasing. In a further trouble-free course of the therapy the signals S1 and S2 then remain constant, which is indicated only briefly in FIG. 3.

FIG. 3 shows another time interval 105 during which humidity penetrates from outside or external leakage occurs outside the housing 4. In these cases both sensors 11 and 12 determine an increase in humidity and both signals S1 and S2 are increasing. Due to the simultaneous increase of both signals S1 and S2, internal leakage, i.e. escape of dialysis fluid from the dialysis fluid system into the housing 4, can be safely excluded. In a subsequent plausibility check in the time interval 106 the machine is operated—as described already before with reference to the time interval 103—with reversed flow direction, wherein in the case of external leakage the sensor values S1 and S2 remain unchanged.

It is finally referred to the fact that instead of the afore-described humidity sensors for direct detection of the liquid share in the air also further or other parameters of the air which allow drawing conclusions to the air humidity inside the housing 4 vis-à-vis the ambient air can be detected by sensors. For example, the temperature which is substantially constant during normal operation of the machine but varies upon occurring increase in air humidity can be measured. Also, plural equal or different sensors can be arranged at the ventilation apertures and/or inside the housing 4 so as to even obtain indications of leakage positions, where necessary.

Finally it is sufficient in the simplest case to arrange a humidity sensor only at the outlet aperture. In this case the humidity content of the ambient air could be measured and stored via said sensor before the start of treatment, because this humidity value does not vary or varies only very slowly. Upon the start of treatment then the only sensor measures the humidity share of the exhaust air, whereupon the current measured value is compared to the value stored in advance.

Summing up, an extracorporeal blood treatment machine, preferably dialysis machine, comprising leakage detection as well as a method of detecting leakages in the dialysis fluid circuit of the extracorporeal blood treatment machine is disclosed, wherein at least part of the dialysis fluid system to be monitored in terms of leakage is accommodated in a housing preferably hermetically sealed against the ambience and the housing is or can be ventilated in a controlled manner, and wherein a parameter, preferably air humidity of the air flowing into the housing, is compared to a corresponding parameter, preferably air humidity of the air flowing out of the housing, so as to conclude the presence of leakage from a possibly occurring difference.

What is claimed:

1. A method of detecting leakage in a dialysis fluid system of an extracorporeal blood treatment machine in which a housing including a first ventilation aperture and a second ventilation aperture and otherwise being hermetically sealed contains at least part of the dialysis fluid system to be detected in terms of leakage, the method comprising:
    ventilating the housing via the ventilation apertures,
    detecting at least one parameter of inlet air supplied to the housing and of outlet air discharged from the housing;
    comparing the inlet air and the outlet air detected parameters to identify a difference; and
    determining a humidity input to the housing which does not originate from the ambient air from the identified difference.

2. The method according to claim 1, wherein the treatment machine is a dialysis machine.

3. The method according to claim 1, wherein the at least one parameter includes at least one of air mass, temperature or humidity.

4. The method according to claim 1, wherein the at least one parameter of the inlet air flowing into the housing or the outlet air flowing out of the housing are detected in discrete measuring cycles.

5. The method according to claim 1, further comprising, when the at least one parameter is indicative of leakage, performing a plausibility check by reversing flow of the air through the housing and comparing the at least one parameter after the change in flow direction to the at least one parameter indicative of leakage preceding the change in flow direction.

6. The method according to claim 1, wherein the ventilation of the housing is stopped or reduced for a time interval before a measuring cycle.

7. The method according to claim 6, wherein a subsequent measurement is performed at a low flow rate.

8. The method according to claim 1, wherein a subsequent measurement is performed at a low flow rate.

9. The method according to claim 8, wherein the low flow rate is insufficient for cooling the machine.

10. The method according to claim 1, further comprising, before a therapy, calibrating the machine by passing air in an initial flow direction through the housing, detecting a first measuring value for air passing in the initial flow direction, reversing the direction of air flow, detecting a second measuring value for air passing in the reversed flow direction, and comparing the first and second measured values.

11. The method according to claim 10, wherein a difference between the first and second measured values is stored and used as a correction factor for subsequent measurements.

* * * * *